(12) United States Patent
Manoux et al.

(10) Patent No.: US 8,701,960 B1
(45) Date of Patent: Apr. 22, 2014

(54) SURGICAL STAPLER WITH REDUCED CLAMP GAP FOR INSERTION

(75) Inventors: Philipe R. Manoux, San Francisco, CA (US); Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 0 days.

(21) Appl. No.: 12/489,397

(22) Filed: Jun. 22, 2009

(51) Int. Cl.
*A61B 17/068* (2006.01)

(52) U.S. Cl.
USPC .......................... 227/175.1; 227/19

(58) Field of Classification Search
USPC ............... 227/19, 175.1, 178.1, 180.1, 176.1
See application file for complete search history.

(56) References Cited

U.S. PATENT DOCUMENTS

| | | |
|---|---|---|
| 3,581,551 A | 6/1971 | Wilkinson |
| 3,650,453 A | 3/1972 | Smith, Jr. |
| 3,899,914 A | 8/1975 | Akiyama |
| 4,086,926 A | 5/1978 | Green et al. |
| 4,228,895 A | 10/1980 | Larkin |
| 4,475,679 A | 10/1984 | Fleury, Jr. |
| 4,589,416 A | 5/1986 | Green |
| 4,608,981 A | 9/1986 | Rothfuss et al. |
| 4,633,861 A | 1/1987 | Chow et al. |
| 4,762,260 A | 8/1988 | Richards et al. |
| 4,969,591 A | 11/1990 | Richards et al. |
| 5,156,315 A | 10/1992 | Green et al. |
| 5,192,288 A | 3/1993 | Thompson et al. |
| 5,307,976 A * | 5/1994 | Olson et al. ............... 227/175.3 |
| 5,336,232 A * | 8/1994 | Green et al. ................ 606/151 |
| 5,358,506 A * | 10/1994 | Green et al. ................ 606/151 |
| 5,413,272 A | 5/1995 | Green et al. |
| 5,441,193 A | 8/1995 | Gravener |
| 5,476,206 A | 12/1995 | Green et al. |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

Gong, Shao W., "Perfectly flexible mechanism and integrated mechanism system design", *Mechanism and Machine Theory* 39 (2004), (Nov. 2004),1155-1174.

(Continued)

*Primary Examiner* — Thanh Truong
*Assistant Examiner* — Andrew M Tecco
(74) *Attorney, Agent, or Firm* — Cardica, Inc.

(57) ABSTRACT

A surgical apparatus may include a staple holder, an anvil connected to and movable relative to the staple holder, and at least one axle extending outward from the anvil; and an overtube slidable relative to the end effector, the overtube including at least one slot defined therein; where each slot receives a corresponding axle. A surgical method for treating tissue of a patient may include providing an end effector that includes a staple holder and an anvil connected to and movable relative to the staple holder, and an overtube slidable relative to said end effector, making an incision in the patient; inserting the end effector and at least part of the overtube through the incision in a first, insertion configuration in which substantially no gap exists between the anvil and staple holder, and moving the overtube relative to the end effector to open the end effector to a second, unclamped position where at least part of the anvil is spaced apart from the staple holder.

4 Claims, 1 Drawing Sheet

(56) References Cited

U.S. PATENT DOCUMENTS

| | | | |
|---|---|---|---|
| 5,531,744 A | 7/1996 | Nardella et al. | |
| 5,624,452 A | 4/1997 | Yates | |
| 5,655,698 A | 8/1997 | Yoon | |
| 5,662,260 A | 9/1997 | Yoon | |
| 5,692,668 A * | 12/1997 | Schulze et al. | 227/175.1 |
| 5,693,051 A | 12/1997 | Schulze et al. | |
| 5,697,542 A * | 12/1997 | Knodel et al. | 227/175.1 |
| 5,716,366 A | 2/1998 | Yates | |
| 5,769,303 A * | 6/1998 | Knodel et al. | 227/176.1 |
| 5,779,131 A * | 7/1998 | Knodel et al. | 227/176.1 |
| 5,779,132 A * | 7/1998 | Knodel et al. | 227/176.1 |
| 5,810,855 A | 9/1998 | Rayburn et al. | |
| 5,814,055 A * | 9/1998 | Knodel et al. | 606/151 |
| 5,816,471 A | 10/1998 | Plyley et al. | |
| 5,833,695 A | 11/1998 | Yoon | |
| 5,855,311 A | 1/1999 | Hamblin et al. | |
| 5,894,979 A | 4/1999 | Powell | |
| 5,918,791 A * | 7/1999 | Sorrentino et al. | 227/175.3 |
| 5,964,774 A | 10/1999 | McKean et al. | |
| 6,004,335 A | 12/1999 | Vaitekunas et al. | |
| 6,086,586 A | 7/2000 | Hooven | |
| 6,306,149 B1 | 10/2001 | Meade | |
| 6,391,038 B2 | 5/2002 | Vargas et al. | |
| 6,602,252 B2 | 8/2003 | Mollenauer | |
| 6,716,232 B1 * | 4/2004 | Vidal et al. | 606/205 |
| 6,817,508 B1 | 11/2004 | Racenet et al. | |
| 6,821,273 B2 | 11/2004 | Mollenauer | |
| 6,843,403 B2 * | 1/2005 | Whitman | 227/176.1 |
| 6,905,497 B2 | 6/2005 | Truckai et al. | |
| 6,926,716 B2 | 8/2005 | Baker et al. | |
| 6,994,714 B2 | 2/2006 | Vargas et al. | |
| 7,001,408 B2 * | 2/2006 | Knodel et al. | 606/207 |
| 7,011,657 B2 | 3/2006 | Truckai et al. | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,128,253 B2 * | 10/2006 | Mastri et al. | 227/176.1 |
| 7,140,527 B2 | 11/2006 | Ehrenfels et al. | |
| 7,168,604 B2 | 1/2007 | Milliman et al. | |
| 7,169,146 B2 | 1/2007 | Truckai et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,311,709 B2 | 12/2007 | Truckai et al. | |
| 7,381,209 B2 | 6/2008 | Truckai et al. | |
| 7,617,961 B2 * | 11/2009 | Viola | 227/175.1 |
| 7,794,461 B2 | 9/2010 | Eder | |
| 7,875,029 B1 | 1/2011 | Hausen | |
| 2003/0045890 A1 | 3/2003 | Crainich | |
| 2003/0114851 A1 | 6/2003 | Truckai et al. | |
| 2003/0120284 A1 | 6/2003 | Palacios et al. | |
| 2003/0236551 A1 | 12/2003 | Peterson | |
| 2004/0059362 A1 * | 3/2004 | Knodel et al. | 606/167 |
| 2005/0072827 A1 | 4/2005 | Mollenauer | |
| 2005/0165444 A1 | 7/2005 | Hart et al. | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0064085 A1 | 3/2006 | Schechter et al. | |
| 2006/0151567 A1 | 7/2006 | Roy | |
| 2006/0224158 A1 | 10/2006 | Odom et al. | |
| 2007/0027472 A1 | 2/2007 | Hiles et al. | |
| 2007/0034668 A1 | 2/2007 | Holsten et al. | |
| 2007/0073341 A1 * | 3/2007 | Smith et al. | 606/219 |
| 2007/0083234 A1 | 4/2007 | Shelton et al. | |
| 2007/0102472 A1 | 5/2007 | Shelton | |
| 2007/0118163 A1 | 5/2007 | Boudreaux et al. | |
| 2007/0125828 A1 | 6/2007 | Rethy et al. | |
| 2007/0145096 A1 | 6/2007 | Viola et al. | |
| 2007/0175950 A1 * | 8/2007 | Shelton et al. | 227/176.1 |
| 2007/0213711 A1 | 9/2007 | Eder et al. | |
| 2008/0110958 A1 | 5/2008 | McKenna et al. | |
| 2008/0172086 A1 | 7/2008 | Hillstead et al. | |
| 2009/0065552 A1 * | 3/2009 | Knodel et al. | 227/180.1 |
| 2009/0095790 A1 | 4/2009 | Whitman et al. | |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |
| WO | WO-2008/039238 | 4/2008 |

OTHER PUBLICATIONS

Lim, Jonas J., et al., "A review of mechanism used in laparascopic surgical instruments", *Mechanism and Machine Theory* 38, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

"International Preliminary Report on Patentability", PCT/US2010/020867, Aug. 11, 2011.

"Notification of Transmittal of ISR and Written Opinion", WO 2009/033057, Apr. 29, 2009.

"International Search Report", WO 2009/033057, Apr. 29, 2009.

"Written Opinion of the International Searching Authority", WO 2009/033057, Apr. 29, 2009.

"Cardica Microcutter Implant Delivery Device 510(k), Cover Sheet, Table 10.1, "Substantial Equivalence Comparison," and Section 12, "Substantial Equivalence Discussion"", Oct. 18, 2010.

* cited by examiner

SURGICAL STAPLER WITH REDUCED CLAMP GAP FOR INSERTION

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. The surgeon inserts the endocutter through a trocar or other port or incision in the body, orients the end of the endocutter around the tissue to be transected, and compresses the anvil and cartridge together to clamp the tissue. Then, a row or rows of staples are deployed on either side of the transection line, and a blade is advanced along the transection line to divide the tissue. Traditionally, it has been important to maintain a substantially constant gap between the anvil and the cartridge for proper staple formation. A staple urged outward from the cartridge or other staple holder is designed to encounter a staple pocket or other feature in the anvil at a certain point in its travel. If the staple encounters that staple pocket or other feature in the anvil too soon or too late, the staple may be malformed. For example, if the gap is too large, the staple may not be completely formed. As another example, if the gap is too small, the staple may be crushed.

BRIEF DESCRIPTION OF THE DRAWINGS

The use of the same reference symbols in different figures indicates similar or identical items.

DETAILED DESCRIPTION

U.S. Patent Application Publication No. 2009/0065552, published on Mar. 12, 2009 (the "Endocutter Document"), is hereby incorporated by reference herein in its entirety.

Figure 1:
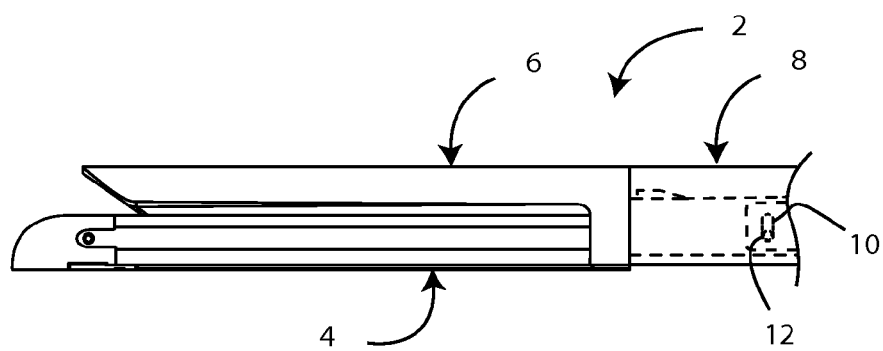
FIG. 1 is a side view of an exemplary staple holder and anvil in a first, delivery configuration with no gap therebetween.

Referring to FIG. 1, an end effector 2 may include a staple holder 4 movable relative to an anvil 6. The staple holder 4 and anvil 6 may be configured substantially as set forth in the Endocutter Document, as modified by the contents of this document. The proximal end of the end effector 2 may be slidably held within an overtube 8. The proximal end of the end effector 2 may extend into the distal end of the overtube 8. The staple holder 4 may include at least one generally vertically-oriented slot 10 defined therein, as viewed from the side. Advantageously, one slot 10 is defined in each side of the staple holder 4, in proximity to the proximal end of the staple holder 4. Alternately, a different number of slots 10 is provided, and/or the location of at least one slot 10 is different. Alternately, at least one slot 10 may be oriented other than generally vertically. An axle 12 extends outward from the anvil 6 into each slot 10. Each axle 12 is slidable within the corresponding slot 10.

Initially, the end effector 2 may be in a first configuration for insertion through a trocar port or other opening in a patient, where substantially no gap exists between the anvil 6 and the staple holder 4. This distance between the anvil 6 and the staple holder 4 optionally may be referred to as a "zero gap." In the first, insertion configuration, each axle 12 may be located at or near the bottom of the corresponding slot 10, in order to minimize the gap between the anvil 6 and the staple holder 4. When the end effector 2 is in the first, insertion configuration, the outer dimensions of the end effector 2 may be equal to or less than the outer dimensions of the overtube 8. That is, the outer dimensions of the end effector 2 may fit within the perimeter of the distal end of the overtube 8 as viewed on end. In this way, the cross-sectional area of the end effector 2 is minimized. Alternately, the end effector 2 may be sized or shaped differently in the first, insertion configuration. At least part of the overtube 8 may be inserted into the patient along with the end effector 2.

Figure 2:
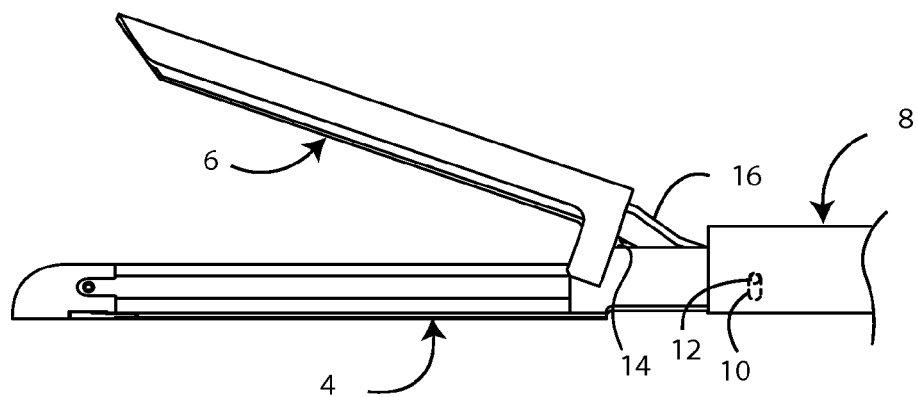
FIG. 2 is a side view of the staple holder and anvil of FIG. 1 in a second, unclamped configuration.

Referring also to FIG. 2, after insertion into the patient, the end effector 2 may be opened to a second, unclamped configuration in any suitable manner. As one example, the overtube 8 may be withdrawn proximally relative to the end effector 2. The anvil 6 may be pivotable upward relative to the staple holder 4, and/or the anvil 6 may be biased upward relative to the staple holder 4 such as by a leaf spring or compression spring 14. As the overtube 8 is withdrawn proximally, that spring 14 pushes the anvil 6 upward relative to the staple holder 4. The anvil 6 may be pivotally connected to the staple holder 4 such that the upward bias of the spring 14 pushes the distal end of the anvil 6 upward. (The use of terms such as "upward" in this document refers to the orientation of parts on the page, and in no way limits the orientation of the device in use.) As the anvil 6 is pushed upward, each axle 12 is also pushed upward within the corresponding slot 10. Each axle 12 may be pushed upward to the upper end of the corresponding slot 10, or to a location between the upper and lower ends of the slot 10. As another example, the anvil 6 is not biased relative to the staple holder 4, and a mechanical linkage (not shown) or other mechanism acts to push the distal end of the anvil 6 upward as the overtube 8 is withdrawn proximally relative to the end effector 2. As the anvil 6 is urged upward by the linkage or other mechanism, each axle 12 is also pushed upward within the corresponding slot 10. Each axle 12 may be pushed upward to the upper end of the corresponding slot 10, or to a location between the upper and lower ends of the slot 10. Where each axle 12 is located in the upper end of the corresponding slot 10, the end effector 2 can open to its widest position.

Figure 3:
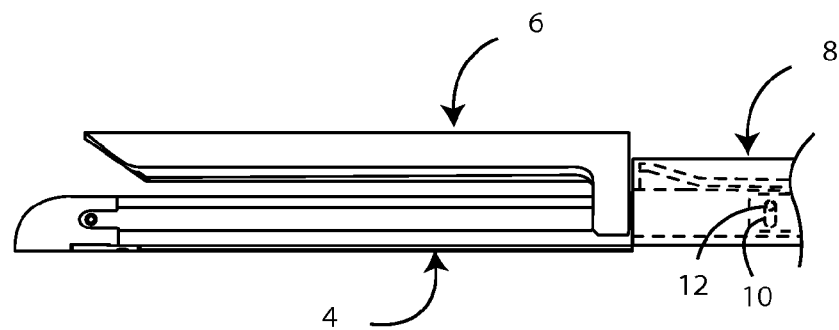
FIG. 3 is a side view of the staple holder and anvil of FIG. 1 in a third, clamped configuration with a gap therebetween.

The opened end effector 2 in the second, unclamped position is moved relative to tissue to be treated in order to place the anvil 6 on one side of that tissue and the staple holder 4 on the other side. The end effector 2 is then moved to the third, clamped position. Referring also to FIG. 3, the overtube 8 is advanced distally relative to the end effector 2. As the overtube 8 advances, the distal end of the overtube 8 encounters an angled ramp 16 of the anvil 6 on the upper surface of the anvil 6. Alternately, the ramp 16 is located on a different surface of the anvil 6, and/or more than one ramp 16 is provided. The ramp 16 is angled or curved downward proximally. As the overtube 8 contacts that ramp 16, further distal motion of that overtube 8 pushes the anvil 6 downward. Where the anvil 6 is rotationally connected to the staple holder 4, such as at the axles 12, the anvil 6 rotates such that the distal end of the anvil 6 moves closer to the staple holder 4. The anvil 6 moves downward, compressing tissue between the anvil 6 and the staple holder 4. The thickness of the tissue stops the clamping motion of the end effector 2. Where the tissue is thick, each axle 12 may be located at the upper end of the corresponding slot 10 when the end effector is in the third, clamped position of FIG. 3. Where the tissue is thinner, each axle 12 may be located in the corresponding slot 10 between the upper and lower ends thereof. That is, each axle 12 may float in the corresponding slot 10, and the position of the axle in that slot 10 is determined by the thickness of the clamped tissue. After the tissue is treated, the end effector 2 is moved back to the second, unclamped position of FIG. 1 by retracting the overtube 8 proximally relative to the end effector 2. The end effector 2 may then be moved back to the third, clamped position to treat tissue in a different location; if so, additional staples may be advanced into the staple holder 4 as set forth in the Endocutter Document. Alternately, if treatment of tissue is complete, the overtube 8 may be advanced distally relative to the end effector 2. Without tissue located between the anvil 6 and the staple holder 4, as the overtube 8 advances distally relative to the end effector 2, the distal end of the overtube 8 encounters the ramp 16 and urges the anvil 6 downward to the first, insertion configuration with substantially no gap between the anvil 6 and staple holder 4. The absence of a gap between the anvil 6 and the staple holder 4 results from the absence of tissue between the anvil 6 and staple holder 4, allowing the anvil 6 and staple holder 4 to move together to the first, insertion configuration without resistance from tissue.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus, comprising:
    an end effector, comprising;
        a staple holder including two sides and at least one vertically-oriented slot defined in each of said two sides, wherein said vertically-oriented slots have a length that is oriented vertically relative to a longitudinal axis of said end effector;
        an anvil pivotally connected at a proximal end to said staple holder, said anvil comprising a ramp at the proximal end and two lateral sides and being movable from a first, insertion configuration relative to said staple holder for insertion through an opening in a patient, in which no gap exists between said anvil and said staple holder, to a second, unclamped configuration, in which at least part of said anvil is spaced apart from said staple holder and a first gap is present between said anvil and said staple holder and in which said end effector may be moved relative to tissue to place said anvil on one side of the tissue and said staple holder on an opposite side of the tissue, to a third, clamped configuration, in which said end effector compresses the tissue between said anvil and said staple holder and in which a second gap is present between said anvil and said staple holder, wherein the first gap is larger than the second gap;
        only one axle extending laterally outward from the anvil, wherein opposite ends of the axle extend from each of said two lateral sides of said anvil into one of the vertically-oriented slots; and
        a spring disposed between said anvil and said staple holder to push a distal end of said anvil upward, relative to said staple holder;
        wherein each of said vertically-oriented slots receives one of said opposite ends of said axle, wherein said axle is moveable within the slots, and wherein said vertically-oriented slots allow for only vertical movement of said axle relative to said longitudinal axis of said end effector;
        wherein, when said anvil is in the first, insertion configuration relative to said staple holder, said axle is located at a bottommost position within each of said slots, when said anvil is in the second, unclamped configuration relative to said staple holder, said axle is located at a topmost position within each of said slots, and when said anvil is in the third, clamped configuration relative to said staple holder, said axle is located at the topmost position within each of said slots or between the topmost and the bottommost position within each of said slots; and
    an overtube slidable longitudinally over a proximal portion of said end effector such that contact between said overtube and said ramp of said anvil urges said anvil toward said staple holder and urges said axle to move toward said staple holder within said slots.

2. The surgical apparatus of claim 1, wherein said spring comprises at least one of a leaf spring or a compression spring.

3. The surgical apparatus of claim 1, wherein an outer dimension of the end effector fits within a perimeter of a distal end of the overtube.

4. The surgical apparatus of claim 1, wherein a position of said axle within each of said slots is determined by a distance between opposing surfaces of the anvil and the staple holder when said overtube and said ramp of said anvil urges said anvil toward said staple holder.

\* \* \* \* \*